United States Patent [19]

Hill

[11] Patent Number: 5,643,183
[45] Date of Patent: Jul. 1, 1997

[54] WATERPROOF COVER FOR CASTS AND BANDAGES

[76] Inventor: Joseph C. Hill, 41 High Ridge Rd., Boxford, Mass. 01921

[21] Appl. No.: 496,362

[22] Filed: Jun. 29, 1995

[51] Int. Cl.$^6$ ..................................................... A61F 5/00
[52] U.S. Cl. ................................................................ 602/3
[58] Field of Search ........................................ 602/3, 4, 5

[56] References Cited

U.S. PATENT DOCUMENTS

| | | | |
|---|---|---|---|
| 3,934,582 | 1/1976 | Gorrie | 602/4 |
| 4,019,506 | 4/1977 | Eschmann | 602/4 |
| 4,254,765 | 3/1981 | Brown et al. | 602/3 |
| 4,363,317 | 12/1982 | Broucek | 602/3 |
| 4,523,586 | 6/1985 | Couri | 602/3 |
| 4,911,151 | 3/1990 | Rankin et al. | 602/3 |
| 4,986,265 | 1/1991 | Caponi | 602/3 |
| 5,342,287 | 8/1994 | Jernoiu | 602/3 |

*Primary Examiner*—Richard J. Apley
*Assistant Examiner*—Kim M. Lee

[57] ABSTRACT

A waterproof cover for casts and bandages on extremities is disclosed. The cover includes an elongated sleeve of transparent polyethylene having a thickness between about 0.001 and 0.006 inches and a length greater than its width. The sleeve has a face side and an obverse side and a distal end and a proximal end. It is hermetically sealed at its distal end thus forming a waterproof cover. A hook and loop fastener is used for affixing the cover on the extremity. A first strip of the hook and loop fastener is disposed on the proximal end of the face side of the sleeve, the first strip having an array of plastic hooks disposed thereon. The first strip extends substantially across the entire width of the face side and the hooks face outwardly from the sleeve. A second strip of loops is disposed on the proximal end of the obverse side. A covering of soft fleece is disposed on the face side. The second strip has a length greater than the width of the sleeve whereby to form extensions to engage the hooks on the first strip. The second strip is joined to the obverse side at its middle thereby leaving the distal ends of the second strip to be unrestricted in movement and to allow portions of the obverse side to be folded and gathered within the sleeve and secured in place by the second strip, thereby to form a water resistant cover when placed upon an extremity.

13 Claims, 1 Drawing Sheet

WATERPROOF COVER FOR CASTS AND BANDAGES

FIELD OF THE INVENTION

The present invention relates to a waterproof covering for bandages and casts disposed on extremities. Particularly, the present invention relates to an elongated sleeve of waterproof plastic to enclose the bandaged or casted extremity. The sleeve has a sealing arrangement to retard or prevent penetration of water when the wearer is bathing or showering. Especially, the present invention relates to a reusable, waterproof cover made of a tough, transparent plastic material that can be easily secured with one hand on the extremity over the cast.

BACKGROUND OF THE INVENTION

Casts and bandages are placed on extremities for lengthy periods of time and can be a source of considerable discomfort. Since casts or bandages should be kept dry while they are on the extremity, bathing, showering, and the like, are difficult. If water soaks into the cast or bandage or penetrates beneath it, the patient will experience discomfort in the form of itching, infection and odor emissions.

Covers for casts and bandages constructed of plastic materials are well known to the art. For example, the device shown in U.S. Pat. No. 5,342,286, discloses a sack-like, water-impervious covering which includes an upper lip with perforations which extend parallel to the opening. An adhesive strip extends over the entire width of the lip from one end to the other. The adhesive strip is covered by a removable sheet to protect the adhesive prior to use. In use, the perforation is torn to separate the lip from the sack and form a tie member. The adhesive protection sheet is removed and the extremity is inserted into the sack-like covering. A securing portion is then is adhered to the surface of the extremity and the opening is gathered around the extremity so that the tie member can be used to encircle the gathering to cover the extremity and prevent the entry of water. Such devices, however, are not reusable since once the adhesive strip is exposed by removing the sheet and the cover is gathered to tighten it around the extremity, the only way the cover can be removed is to destroy it. Since casts are kept on for generally four to six weeks, a significant number of these covers must be used if the wearer wants to bathe or shower. Also, placement of the adhesive around the extremity is sometimes difficult because a single slip will cause permanent improper disposition of the cover. Attempting to reseat the adhesive most frequently tears the plastic and renders the cover unusable. Moreover, I have found the use of hook and loop fasteners enables one to use a single diameter cover for a wide range of leg or arm diameters, thereby eliminating requirements for many different models for differently sized extremities.

One of the more common and inexpensive ways to cover casts and bandages is to use a trash bag and place a rubber band or duct tape around the opening to exclude water. Rubber bands are not overly effective because they frequently do not adequately gather all of the folds of the trash bag, especially since the folds usually randomly encircle the extremity because of the large diameter of the opening relative to the diameter of the extremity being protected. Such random folds provide access for the entry of water. Duct tape is a more effective sealing mechanism but a trash bag must be destroyed each time the duct tape is removed because of the strength of the adhesive.

SUMMARY OF THE INVENTION

I have discovered a waterproof cover for casts or bandages on extremities. It includes an elongated sleeve of waterproof plastic having a length greater than its width, thus to cover a cast on either the leg or the arm without providing a substantial number of folds. Generally, the cover is provided in two sizes, one to accommodate the leg and another to accommodate the arm. Of course, covers can be made for lesser extremities such as the foot, the ankle and foot, the hand or the hand and foot. The sleeve has a diameter at least about 20% more than the diameter of an average thigh or leg (depending upon which limb is to be covered). It has a length a bit greater than the length of an average arm to the tip of the fingers or from the top of the thigh to the toe. The length is not particularly critical, however, so long as the cover can be worn comfortably and safely. One end of the cover is sealed to form a sack and prevent passage of water. A first strip constituting half of a hook and loop fastener, commonly a Velcro® fastener, is disposed on one side of the other end of the sleeve. The portion of the hook and loop strip used has an adhesive back with hook elements, as is well known. The hooks are arranged to face outwardly from the sleeve. A second strip constituting the other half of the hook and loop fastener is disposed on the opposite side of the sleeve. The second strip has a medial section with two distal ends. The second strip is the loop portion of the hook and loop fastener. The second strip has a medial portion which is attached to the sleeve at the middle of the opposite side of the sleeve. The second strip has a length greater than the width of the sleeve and its loops can engage the hooks on the first strip. In use, after the sleeve is disposed on the extremity, the excess sleeve material is folded and gathered within the sleeve and secured in place by the second strip. The tightness of the second strip can be adjusted around the extremity to prevent the passage of water during bathing. Preferably, the first strip and the third strip are disposed a predetermined distance from the proximal end of the cover, generally about 0.25 inches, so as to form a lip to accommodate for slippage of the second strip during bathing and provide additional protection against the entry of water.

The many other objects, features and advantages will become manifest to those with ordinary skill in the art upon reading the following specification when taken in conjunction with the accompanying drawings.

DESCRIPTION OF THE PREFERRED EMBODIMENT

Figure 1:
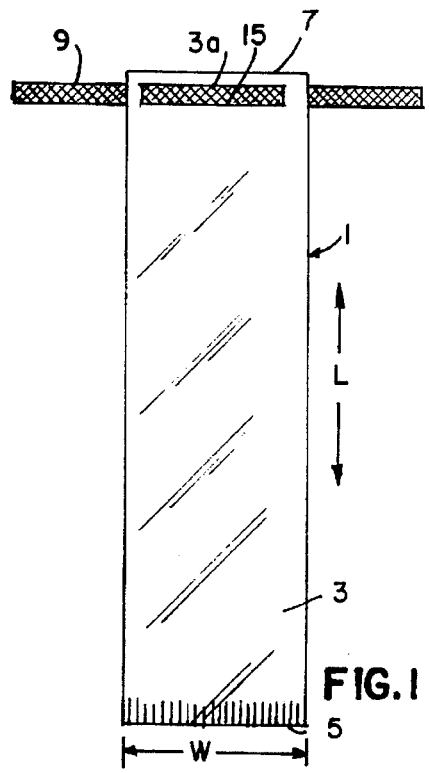
FIG. 1 is an elevational view of the front side of the cover of the present invention.
Figure 2:
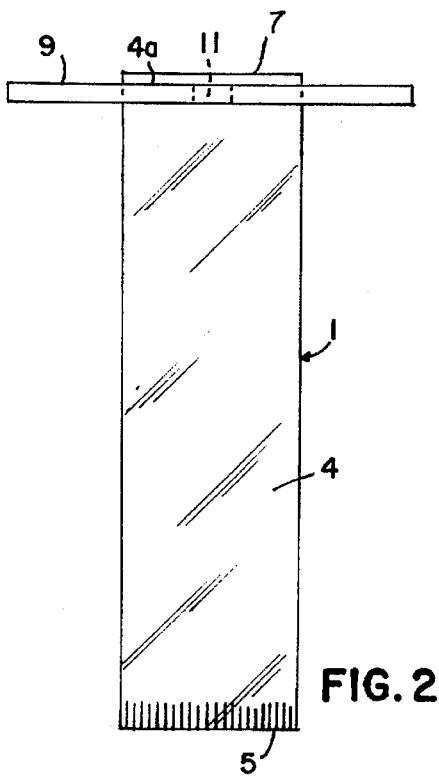
FIG. 2 is an elevational view of the obverse side of the cover of the present invention.

Referring now to FIGS. 1 and 2 of the drawings, the cover of the present invention includes an elongated sleeve 1 in which the length L is greater than width W. The sleeve 1 has a face side 3 and an obverse side 4. The sleeve 1 also has a sealed distal end 5 and an open proximal end 7. The sealed distal end 5 is formed by heat sealing the distal edges of the sleeve 1 together in a conventional manner. An edge between the face and obverse sides can be heat sealed together to form the sleeve or tubular stock can be used.

Preferably, the cover 1 is made of waterproof plastic material, usually polyethylene, with a thickness between about 0.001 and 0.006 inches. The polyethylene is transparent so the user can see if water is leaking into the cover and if the cast or bandage is being properly protected. By using transparent polyethylene, the cover is reusable many times, thus reducing the cost of protection. Moreover, the polyethylene can be easily adjusted during use to provide the wearer with comfort while bathing. Such polyethylene also enables the manufacturer to readily fold the cover into a flat, square or rectangular shape to provide for packaging in a thin transparent envelope with a hole on top, commonly called a rack pack.

Hook and loop fasteners are used to secure the cover around the user's extremity that is to be protected. Such fasteners are formed of two members, one of which has hooks on it and the other of which has loops. In the present invention, strips of Velcro® are preferably used. Commonly, the hooks are plastic and arranged in rows on a plastic backing and the loops are a soft and fleece-like, densely packed in an array and also disposed on a plastic backing.

As shown in FIGS. 1 and 2, a first strip 9 of the fastener is formed of loops. It is disposed on the face side 4 of the cover 1. The loops of the first strip 9 are attached to about the middle of the obverse side 4 of the sleeve with a small strip 11 of hooks. The first strip 9 is about 1.25 to 1.75 times longer than the width W of the cover 1. This relative dimension is important for the proper securing of the cover 1. The small strip 11 is disposed approximately at the middle of the obverse side 4 of the cover 1. The hooks of the small strip 11 can grasp the loops of the fleece in the first strip 9, but the first strip 9 can be removed entirely from the cover 1 as needed.

A strip 15 of hooks is adhesively attached and disposed on the face side 3 of the cover 1. Preferably, the strip 15 is substantially as long as the width W of the cover.

Figure 3:
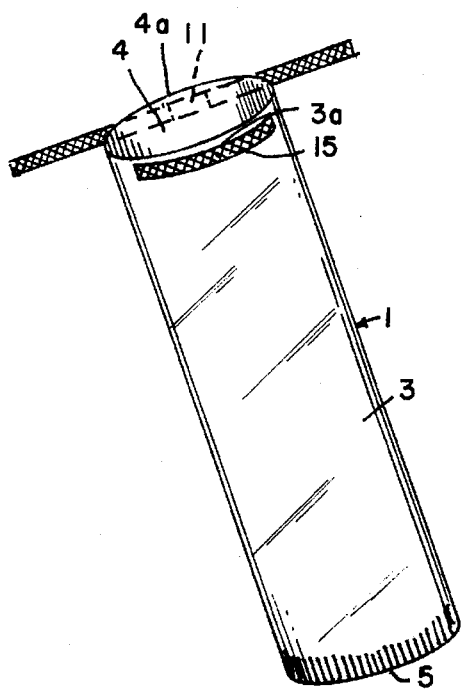
FIG. 3 is a perspective view illustrating the cover in an open position ready to receive a casted extremity.

Referring to FIG. 3, the face side 3 of the cover 1 is separated from the obverse side 4. As shown, both the small strip 11 and the strip 15 are disposed a predetermined distance from the proximal end of the cover 1 whereby to form lips 3a and 4a. Lips 3a–4a are provided so that when the first strip 15 is wrapped around the face side 3 of the cover 1, they will prevent the first strip 9 from slipping over the edge whereby to render the seal less effective.

Figure 4:
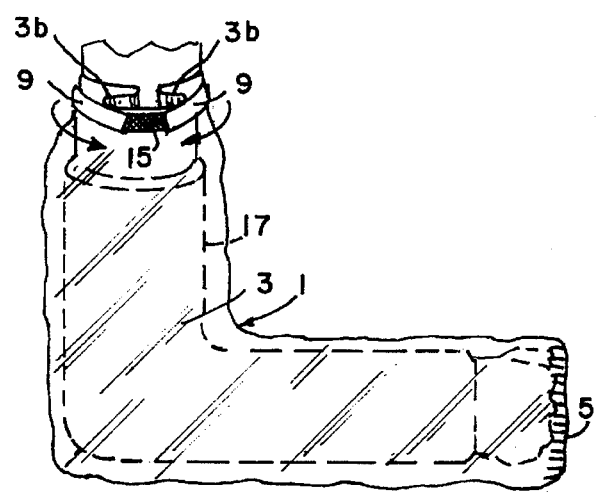
FIG. 4 is a side elevational view of the cover illustrating its disposition on an arm within the cover and with the excess cover material correctly folded immediately prior to fully tightening and securing the fastener.

As shown in FIG. 4, excess portions of the face side 3 are folded under the first strip 9. When the first strip 9 is wrapped tightly and adhered to the strip 15, a water-resistant seal will be formed. Folds 3b will snugly fit beneath the fleece of the first strip 9.

In use, an extremity is slipped into the cover 1 with the top of the cover 1 as close to the shoulder (or hip if that is being protected) as possible. Excess cover 3b is then folded under the first strip 9 and the first strip 9 is wrapped around one side and attached to the strip 15. The process is repeated so that both ends of the first strip 9 are snugly disposed around the cover 1. Each strip can be further adjusted, as needed, to ensure a good seal. To remove or adjust the cover during use, water should be turned off and the lips 3a, 4a should be wiped dry. The cover 1 is then removed from the extremity by pulling the ends of the first strip 9 from the strip 15. The cover is then removed from the extremity and dried for reuse. Quite importantly, the use of the fasteners on the cover 1 enables the user to reuse the cover 1 many times while the cast is in place. Devices which use adhesives can only be used once and thus lack in the ecological benefits provided by the cover of the present invention.

While the cover of the present invention is primarily useful for covering casts and bandages it is also useful for protecting skin disorders or covering heparin locks which have been placed on an extremity to enable the wearer to take showers easily.

While it is apparent that changes and modifications can be made within the spirit and scope of the present invention, it is my intention, however, only to be limited by the scope of the appended claims.

As my invention I claim:

1. A waterproof cover for casts and bandages to be placed on extremities of a user said cover comprising:

an elongated sleeve of waterproof plastic, said sleeve having a length greater than its width, said sleeve having a face side (3) and an obverse side (4) and a distal end (5) and a proximal end (7);

means for sealing together the distal ends of the face and obverse sides of said sleeve to form a water tight seal;

a first strip (15) disposed on and permanently attached to the proximal end of the face side of said sleeve, said first strip (15) having an array of plastic hooks disposed thereon, said first strip (15) extending substantially across the entire width of said face side (3) of said sleeve and said hooks facing outwardly from said sleeve;

a second strip (9) disposed on the proximal end (7) of said obverse side (4) of said sleeve, said second strip (9) having a face side, an obverse side and a medial section, said strip further having two distal ends, a covering of soft fleece forming loops disposed on the entire length of said face side of said second strip, said second strip having a length greater than the width of said sleeve, said greater length forming extensions at said distal ends, the fleece on each of said extensions directly engaging the hooks on said first strip (15);

means (11) for joining said medial section of said second strip to said first strip on said obverse side of said sleeve thereby leaving the distal ends of said second strip (9) unrestricted in movement and to allow portions of said obverse side of said sleeve to be folded and gathered about said sleeve directly beneath each of said distal ends of said second strip and secured in place by attaching each of said distal ends of said second strip to said first strip, thereby to form a water resistant cover when placed upon an extremity of a user.

2. The cover according to claim 1 wherein said means for joining is a third strip (11) with hooks on one side thereof and with the other side being attached to said obverse side (4).

3. The cover according to claim 1 wherein said first strip (15) and said third strip (11) are disposed a predetermined distance from the proximal end (7) of said cover whereby to form a lip to accommodate for slippage of said second strip (9) while still providing protection against the entry of water.

4. The cover according to claim 1 wherein the cover is formed of polyethylene.

5. The cover according to claim 1 wherein the plastic forming said cover is transparent.

6. The cover according to claim 1 further including an anti-static coating on said sleeve.

7. The cover according to claim 1 wherein the thickness of the cover is between about 0.001 and 0.006 inches.

8. The cover according to claim 1 wherein the sleeve is formed of tubular plastic, said tube being pressed flat to form side edges which extend from said distal end (5) to said proximal end (7), said proximal end also being flat without wrinkle, whereby said cover can be folded flat for packaging.

9. The cover according to claim 1 wherein the diameter of the sleeve is at least about 20% greater than the average diameter of the extremity to be covered.

10. A waterproof cover for casts and bandages adapted to be placed on extremities of a user, said cover comprising:
- an elongated sleeve (1) of transparent polyethylene having a thickness between about 0.001 and 0.006 inches, said sleeve having a length greater than its width, said sleeve having a face side (3), an obverse side (4), a distal end (5) and a proximal end (6);
- means for sealing together the distal ends of the face and obverse side of said sleeve to form a water tight seal;
- a first strip (15) disposed on and permanently attached to the proximal end of the face side (3) of said sleeve, said first strip (15) having an array of plastic hooks disposed thereon, said first strip (15) extending substantially across the entire width of said face side (3) of said first strip and said hooks facing outwardly from said sleeve;
- a second strip (9) disposed on the proximal end (7) of said obverse side (4), said second strip (9) having a face side, an obverse (4), a medial section, said second strip further having two distal ends, a covering of soft fleece disposed on the entire length of said face side, said second strip having a greater length than the width of said sleeve and extending beyond each side of said obverse side (4) of said sleeve, each distal end of said second strip engaging the hooks on said first strip (15);
- means for joining said medial section of said fleece to said obverse side (4) of said sleeve and leaving the distal ends of said second strip (9) unrestricted in movement and to allow portions of said obverse side (4) to be folded and gathered about said second strip (9) to said first strip (15), thereby to form a water resistant cover when placed upon an extremity of a user.

11. The cover according to claim 10 wherein said means for joining (11) is a third strip with hooks on one side thereof and with the other side said third strip (11) being cemented to said obverse side (4), said first strip (15) and said third strip (11) being disposed a predetermined distance from the proximal end (7) of said cover whereby to form a lip to accommodate for slippage of said second strip (9) while still providing protection against the entry of water.

12. The cover according to claim 10 wherein the sleeve is formed of tubular plastic, said tube being pressed flat to form side edges which extend from said distal end (5) to said proximal end (7), said proximal end also being flat without wrinkles, whereby said cover can be folded flat for packaging.

13. The cover according to claim 10 wherein the diameter of the sleeve is at least about 20% greater than the average diameter of the extremity to be covered.

* * * * *